US005750994A

United States Patent [19]
Schlager

[11] Patent Number: 5,750,994
[45] Date of Patent: May 12, 1998

[54] POSITIVE CORRELATION FILTER SYSTEMS AND METHODS OF USE THEREOF

[75] Inventor: Kenneth J. Schlager, Elm Grove, Wis.

[73] Assignee: Instrumentation Metrics, Inc., Tempe, Ariz.

[21] Appl. No.: 547,145

[22] Filed: Oct. 24, 1995

Related U.S. Application Data

[63] Continuation-in-part of Ser. No. 509,696, Jul. 31, 1995, abandoned.

[51] Int. Cl.$^6$ .......................... G01N 21/35; G01N 33/49
[52] U.S. Cl. .......................... 250/339.11; 250/339.12
[58] Field of Search .................. 250/339.01, 339.11, 250/339.12, 341.8; 128/664

[56] References Cited

U.S. PATENT DOCUMENTS

| 4,306,152 | 12/1981 | Ross et al. | 250/343 |
|---|---|---|---|
| 4,371,785 | 2/1983 | Pedersen | 250/343 |
| 4,427,889 | 1/1984 | Müller . | |

(List continued on next page.)

FOREIGN PATENT DOCUMENTS

| 0 419 223 A2 | 3/1991 | European Pat. Off. . |
| 0 670 143 A1 | 2/1995 | European Pat. Off. . |
| 2244128 | 11/1991 | United Kingdom . |
| WO 92/17765 | 10/1992 | WIPO . |

OTHER PUBLICATIONS

N.M. Faber et al., "Generalized Rank Annihilation Method III: Practical Implementation", *Jrn. of Chemometrics* 8:273–285 (1994).

H.M. Heise et al., "Noninvasive Blood Glucose Sensors Based on Near–Infrared Spectroscopy", *Blackwell Scientific Pub., Inc.* 18(6):439–447 (1994).

SBIR, Phase I, Monthly Technical Progress Report No. 1, Near Infrared Spectral Determination of Human Tissue pH, Contract Number: DAMD17–95–C–5035, Biotronics Technologies, Inc., Mar. 15–Apr. 15, 1995 (Apr. 23, 1995).

SBIR, Phase I, Monthly Technical Progress Report No. 2, Near Infrared Spectral Determination of Human Tissue pH, Contract Number: DAMD17–95–C–5035, Biotronics Tchnologies, Inc., Apr. 15–May 15, 1995 (May 18, 1995).

Small Business Innovation Research (SBIR) Program, Topic Number A94–080, Near Infrared Spectral Determination of Human Tissue pH, Biotronics Technologies, Inc., Jul. 14, 1994.

Award/Contract Number DAMD 17–95–C–5035 dated Mar. 15, 1995, Requisition/Purchase Request/Project No. FORM92–9421–4010, issued by U.S. Army Medical Research Acquisition Activity to contractor Biotronics Technologies Inc.

*Primary Examiner*—Edward J. Glick
*Attorney, Agent, or Firm*—Bozicevic & Reed LLP

[57] ABSTRACT

A number of optically active elements are provided that enable the performance of accurate, dependable chemical analysis in a medium having varying matrix backgrounds and substantial component interferences. Optical transfer cells are provided that include positive correlation filter systems adapted to accept near-IR radiation and to pass a wavelength from that radiation having high correlation with a particular analyte. A near-IR spectrometer apparatus for the measurement of analyte concentration in a complex medium is also provided. The apparatus features an optical transfer cell constructed according to the invention. The apparatus can be used in the non-invasive determination of blood analyte concentrations in a variety of mediums. Methods of measuring the concentration of a blood analyte in a mammalian subject are also provided. The methods entail the use of reflective near-IR radiation to interrogate a medium to obtain spectrally modified radiation. The radiation thus obtained is passed through an optical transfer cell constructed according to the invention to obtain a wavelength having high correlation with an analyte of interest and substantially no correlation with interfering constituents present in the medium.

8 Claims, 2 Drawing Sheets

U.S. PATENT DOCUMENTS

| | | | |
|---|---|---|---|
| 4,655,225 | 4/1987 | Dähne et al. | 128/664 |
| 4,738,535 | 4/1988 | Webster | 356/418 |
| 4,882,492 | 11/1989 | Schlager | 250/345 |
| 4,975,581 | 12/1990 | Robinson et al. . | |
| 5,023,804 | 6/1991 | Hoult | 364/498 |
| 5,070,874 | 12/1991 | Barnes et al. | 128/664 |
| 5,077,476 | 12/1991 | Rosenthal | 250/339.12 |
| 5,086,229 | 2/1992 | Rosenthal et al. . | |
| 5,099,123 | 3/1992 | Harjunmaa | 250/345 |
| 5,218,207 | 6/1993 | Rosenthal | 250/343 |
| 5,222,496 | 6/1993 | Clarke | 356/41 |
| 5,242,602 | 9/1993 | Richardson et al. | 356/300 |
| 5,252,829 | 10/1993 | Nygaard et al. | 250/343 |
| 5,258,620 | 11/1993 | Sueyasu et al. | 250/339.12 |
| 5,267,152 | 11/1993 | Yang et al. . | |
| 5,321,265 | 6/1994 | Block | 250/343 |
| 5,360,004 | 11/1994 | Purdy et al. | 128/664 |
| 5,370,114 | 12/1994 | Wong et al. | 128/664 |
| 5,424,545 | 6/1995 | Block et al. . | |
| 5,460,177 | 10/1995 | Purdy et al. | 250/339.11 X |
| 5,545,897 | 8/1996 | Jack | 250/339.12 |

POSITIVE CORRELATION FILTER SYSTEMS AND METHODS OF USE THEREOF

CROSS-REFERENCE TO RELATED APPLICATIONS

This application is a continuation-in-part of U.S. patent application Ser. No. 08/509,696, filed Jul. 31, 1995, now abandoned, from which priority is claimed pursuant to 35 U.S.C. §120, and which disclosure is hereby incorporated by reference in its entirety.

TECHNICAL FIELD

The present invention relates to a spectrometer device for quantifying target chemical analytes in a complex aqueous medium and methods of use thereof. The invention finds application in a wide range of chemical analyses, and particularly in non-invasive spectrophotometric analysis of blood analytes. One important application of the invention involves the precise measurement of blood glucose using non-invasive sampling techniques.

BACKGROUND OF THE INVENTION

As patient out-care services become more prevalent in modern health care, the need for low-cost, reliable instrumentation becomes more acute, particularly for applications where blood analyte chemistry monitoring must be carried out. One such application is in home-monitoring of blood glucose levels by diabetics.

Diabetes is a major health concern in the United States where it has been estimated that there are upwards of 13 million persons afflicted with the condition. Lipsett, L. (1993) "Statistics: Prevalence, Incidence, Risk Factors and Complications of Diabetes," *American Diabetes Association Bulletin* Apr. 9, 1993. Treatment of the more severe form of the disease, Type I insulin-dependent diabetes (where the pancreas secretes no insulin) requires one or more insulin injections per day. Insulin controls the utilization of glucose or sugar in the blood and prevents hyperglycemia which, if left uncorrected, can lead to ketosis, coma and death.

Hyperglycemia in diabetics has been correlated with several long-term effects of diabetes, such as heart disease, atherosclerosis, blindness, stroke, hypertension and kidney failure. Normally, a person's blood glucose level may vary between 60 and 100 milligrams per deciliter, whereas in a diabetic, the levels may vary from 40 to 500 milligrams per deciliter. Such drastic blood glucose level swings must be avoided in order to prevent the serious complications of the disease. Accordingly, blood glucose concentrations need to be periodically monitored, in some instances up to four times daily, so that diabetics may monitor their blood glucose level and vary caloric intake, diet and insulin accordingly.

Traditional blood glucose monitoring methods require the diabetic to draw a blood sample (e.g., by a finger-tip lance) for each test and to read the glucose level using a glucometer (a spectrophotometer that reads glucose concentrations) or a calorimetric calibration method. Such invasive blood extractions create a painful and tedious burden to the diabetic and expose the diabetic to the possibility of infection, particularly in light of the frequency of testing which is necessary. These considerations can lead to an abatement of the monitoring process by the diabetic.

The value of frequent monitoring of blood glucose as a means to avoid or at least minimize the complications of Type I diabetes has been well established. Further, patients with Type II (non-insulin-dependent) diabetes can benefit from blood glucose monitoring in the control of their disease, however, the inconvenience and traumatic nature of known procedures discourages such monitoring in many patients.

Accordingly, there is a recognized need in the art for a simple and accurate method and apparatus for non-invasively measuring blood analyte concentration, particularly in the context of blood glucose monitoring by diabetics. Various types of apparatus and related methods for non-invasive measurement of glucose concentration and other blood analyte concentrations have been described in the art. Such devices use traditional methods of near infrared (near-IR) analysis based on the measurement of absorbance at one or more specific wavelengths.

U.S. Pat. No. 5,267,152 to Yang et al. describes a non-invasive technique of measuring blood glucose concentration using near-IR radiation diffuse-reflection laser spectroscopy. The device uses only a narrow portion of the IR spectrum referred to as the "water transmission window" (those wavelengths between 1300 and 1900 nm). The optically controlled light is impinged on a tissue source and then collected by an integrating sphere. The collected light is then analyzed and blood glucose concentration is calculated using a stored reference calibration curve.

U.S. Pat. No. 5,086,229 to Rosenthal et al. describes a device for measurement of blood glucose using analysis of near-IR energy following interaction with venous or arterial blood, or following transmission through a blood containing body part. A transmissive technique is described wherein at least one source of near-IR energy (of a selected bandwidth) is provided for passage through a sample. Measurement of glucose concentration is carried out using quantitative analysis algorithms which generally employ ratios and gaps to create mass coefficients of absorption.

U.S. Pat. No. 4,975,581 to Robinson et al. describes a method and apparatus for determining analyte concentration in a biological sample based on a comparison of infrared energy absorption (i.e., differences in absorption at several wavelengths) between a known analyte concentration and a sample. The comparison is performed using partial least squares analysis or other multivariate techniques.

U.S. Pat. No. 4,882,492 to Schlager describes a method and apparatus for non-invasive determination of blood analyte concentrations. Modulated IR radiation is directed against a tissue sample (e.g., an ear lobe) and either passed through the tissue or impinged on a skin surface where it is spectrally modified by a target analyte (glucose). The spectrally modified radiation is then split, wherein one portion is directed through a correlation cell and another through a reference cell. Intensity of the radiation passing through the cells are compared to determine analyte concentration in the sample.

Additionally, similar devices have been described for use in determination of analyte concentrations in complex samples.

U.S. Pat. No. 5,252,829 to Nygaard et al. describes a method and apparatus for measuring the concentration of urea in a milk sample using an infrared attenuation measuring technique, wherein milk samples (of substantially known and constant component concentration) are analyzed for IR attenuation at discrete wavebands where urea, fat, lactose and protein absorb. Multivariate techniques are carried out to determine spectral contributions of each known component using partial least squares algorithm, principal component regression, multiple linear regression or artificial neural network learning. Calibration is carried out by accounting for the component contributions that block the analyte signal of interest (urea). Thus, Nygaard et al. describe a technique of measuring multiple analyte infrared attenuations-and then compensating for the influence of background analytes on the measurement of a selected analyte (e.g., compensating for background contribution to the urea signal).

U.S. Pat. No. 5,242,602 to Richardson et al. describes methods for analyzing aqueous systems to detect multiple active or inactive water treating components. The methods involve determination of the absorbance or emission spectrum of the components over the range of 200 to 2500 nm, and application of chemometrics algorithms to extract segments of the spectral data obtained to quantify multiple performance indicators.

U.S. Pat. No. 4,306,152 to Ross et al. describes an optical fluid analyzer designed to minimize the effect of background absorption (the overall or base level optical absorption of the fluid sample) on the accuracy of measuring a component in a turbid or otherwise hard to analyze liquid sample. The apparatus measures an optical signal at the characteristic optical absorption (of a sample component of interest) and another at a wavelength selected to approximate background absorption and then subtracts to reduce the background component of the signal.

None of the aforementioned devices or methods have been capable of providing low cost, accurate determination of blood analyte concentration in field or home-testing applications. Particularly, known devices have not provided for the accurate determination of blood analyte concentrations in the midst of multiple interferences from other analytes that are active in the same spectral region as the analyte of interest.

SUMMARY OF THE INVENTION

Accordingly, it is a primary object of the invention to address the above-mentioned needs in the art, by providing optically active elements that enable one to perform accurate, dependable chemical analysis in an aqueous medium with varying matrix background and substantial component interferences. The optically active elements allow for optimal analyte measurement at low cost for a wide variety of medical, industrial and environmental applications.

Spectrometers are generally known for use in a wide variety of areas such as medicine, scientific research, industrial applications and the like. In one aspect of the invention, an optical transfer cell is provided for use in spectrometer devices which can be used to quantify target chemical analytes in an aqueous medium. In this regard, the optical transfer cell is particularly intended for use in measurements where there exist complex spectral backgrounds (e.g., where interfering substances introduce significant measurement error), and especially where concentrations of background substances greatly exceed those of a target analyte. The subject optical transfer cell finds application in a wide range of chemical analyte analyses carried out in a diversity of aqueous media.

In one embodiment, an optical transfer cell is provided which comprises a positive correlation filter system. The subject filter system is adapted to accept near-IR radiation and to pass a wavelength from that radiation which is selected to have a high correlation with a particular analyte. The optical transfer cell can thus be used in the measurement of analyte concentrations in complex aqueous media, such as in the measurement of blood analytes in body tissue. In another, related embodiment, a positive correlation filter system is provided that is capable of accepting near-IR radiation and selectively passing a plurality of wavelengths having high correlation with a particular analyte.

In an alternative embodiment, a positive correlation filter system is provided that has been formed from a plurality of filter layers, each layer having a selected optical activity (absorption characteristic), whereby the system is capable of passing a population of wavelengths selected to have high correlation with a particular analyte concentration. In one particularly preferred embodiment, the aforementioned positive correlation filter system has at least one layer that includes wavelength weighting factor means. In this manner, the wavelength weighting factor provides enhanced correlation between a passed wavelength and analyte concentration in a particular medium.

Thus, in order to overcome absorption interference caused by background components in a given sample, the present invention provides a number of positive correlation filter systems which are designed to provide a high correlation with a target analyte and significantly lower correlations with other background absorbing materials. That is, positive correlation filtration relates to the transmission of a pattern of light through an optically active filter which selectively passes "weighted" wavelengths; wherein the passed wavelengths correlate closely with a target analyte concentration in a given sample.

In another aspect of the invention, positive correlation filter systems are synthesized using mathematical optimization techniques such as least squares analysis, linear rotated principal component analysis (RPC), or nonlinear genetic algorithm analysis. Thus, weighting factors can be determined by application of the above-described optimization techniques to an original absorption spectrum of a selected analyte. In preferred embodiments, positive correlation filters are formed from a plurality of layers, each layer having an appropriate absorption characteristic supplied by a weighting factor, wherein the filter selectively passes a population of wavelengths are weighted according to positive correlation to target analyte concentration.

In yet a further aspect of the invention, an apparatus for the accurate measurement of analyte concentration in complex aqueous media is provided. The apparatus includes a source of near-IR radiation, a means for reflectively transmitting near-IR radiation from the source to an aqueous medium which is to be interrogated, and a means for retransmitting spectrally modified radiation reflected from the aqueous medium. The apparatus also includes means for receiving and directing the spectrally modified radiation into a beam path which is communicated to an optical transfer cell disposed within the beam path. The transfer cell comprises a positive correlation filter constructed according to the invention. The subject positive correlation filter is adapted to selectively pass a wavelength from the beam of spectrally modified radiation, wherein the wavelength has high correlation with a selected analyte concentration. The passed wavelength is then communicated to a means for receiving said information and converting the same into a signal which is representative of the intensity of the wavelength (e.g., a photodetector or a near-IR photodiode array), and that signal is transmitted to a means for calculating analyte concentration.

In the practice of the invention, the above-described apparatus can include any of the positive correlation filter systems as described herein. In particular embodiments, the subject devices can be used to measure blood analyte concentration in body tissue. The blood analyte to be measured can be selected from the group of calcium, potassium, sodium, chloride, bicarbonate ($CO_2$), hydrogen ion concentration (pH), glucose, urea (blood urea nitrogen, or BUN), hematocrit and hemoglobin. The source of near-IR radiation preferably supplies radiation including at least wavelengths in the range of approximately 1100 to 2500 nm. In one particularly preferred embodiment, the apparatus can be used in the non-invasive analysis of a blood analyte such as blood glucose.

In an additional aspect of the invention, a non-invasive method of measuring the concentration of a blood analyte in a mammalian subject is provided. The method includes the steps of:

(a) directing near infrared radiation to a source containing the blood analyte;

(b) causing the radiation to be reflected by the source to provide a spectrally modified beam;

(c) directing the modified beam into a path through an optical transfer cell disposed in the beam path. The optical transfer cell includes a positive correlation filter means that is adapted to accept the spectrally modified beam and to pass a wavelength from that beam, wherein that wavelength has been selected to have high correlation with the analyte concentration;

(d) measuring the intensity of the passed wavelength and generating a signal representative of the intensity of the wavelength; and (e) converting the signal into an indication of analyte concentration.

In one case, a non-invasive technique for measuring a blood analyte is provided which enables reflective, transcutaneous tissue measurement of blood glucose in the forearm area. Such measurement gives rise to a more uniform representation of blood glucose than previously possible using transmissive measurements in the finger area.

DETAILED DESCRIPTION OF THE PREFERRED EMBODIMENTS

Before the invention is described in detail, it is to be understood that this invention is not limited to the particular component parts of the devices or methods described, as such may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "an analyte" includes mixtures of analytes, reference to "an optical transfer cell" includes two or more such optical transfer cells, "a means for reflectively transmitting radiation" includes two or more such means, "a wavelength" includes two or more wavelengths, "a chemometrics algorithm" includes two or more such algorithms, and the like.

In this specification and in the claims which follow, reference will be made to a number of terms which shall be defined to have the following meanings:

As used herein, a "reference sample" refers to an aqueous composition comprising a known concentration of an analyte of interest. A "standard" or "calibrant" is a reference sample used for establishing the response of a measurement system to an analyte. As such, a calibration reference is typically any of the standards of various types that indicate whether an analytical instrument is working within prescribed limits and by which adjustments may be made to the analytical measurement system to correct for any deviation from the prescribed limits.

"Calibration" refers to the process of relating an instrumental response to a concentration or property of a targeted matrix with the objective of developing a means to provide accurate and precise predictions in the future. The calibration step produces a direct interpretation of a measurement through a mathematical transformation that models the relationship between a concentration and a spectral response.

Methods of calibration are divided into estimation and classification techniques. "Estimation techniques" relate to the process of predicting the level of analyte concentration, while "classification techniques" determine which one of several predefined groups a sample will belong to. Methods of estimation are particularly useful in applications wherein the measurement of concentration is desired. To calibrate an instrument for estimation, it is necessary to have a set of exemplary measurements with known concentrations referred to as the calibration set (e.g., reference set). This set consists of m samples, each with n instrument variables contained in an m by n matrix (X), and an m by 1 vector (y), containing the concentration. If a priori information indicates the relationship between the measurement and concentration is linear, the process of calibration will attempt to determine an n by 1 transformation or mapping (b), such that $$\hat{y}=Xb$$

is an optimal estimate of y according to a predefined criteria. Estimation techniques are known in the art and include multiple regression, partial least squares regression, principal component regression and rotated principal components regression.

The classification of a measurement is the primary focus of pattern recognition. Assuming a calibration set X, in which the class of each sample is known, methods of classification are used to develop a calibration model that will allow the classification of unknown measurements. Methods of classification are generally known in the art, and include template matching which involves the use of templates and a measurement of similarity, and discriminant analysis that optimizes the separation of samples in a given class through a rotation of measurements.

The general validity of a calibration model can be verified by estimating the concentrations of independent measurements, a "test set," that has not been used in the calibration procedure. When the number of samples available for calibration are limited, the data set can be segmented, wherein part of the data set is used as the training set, and the remaining data used for the test set.

"Chemometrics" relates to the application of mathematical, statistical and pattern recognition techniques in chemical analysis applications. See, e.g., Brown et al. (1990) Anal. Chem. 62:84–101. Chemometrics is practiced herein in the context of developing and using non-invasive medical diagnostic instrumentation that employs advanced signal processing and calibration techniques. Signal processing is used to improve the accessibility of physically significant information in analytical signals. Examples of signal processing techniques include Fourier transformation, first and second derivatives, and digital or adaptive filtering. In the context of chemometrics, "calibration" refers to the process of relating data measurements to a chemical concentration for the purpose of quantification. Particularly, statistical calibrations using chemometric methods can be used to extract specific information from a complex set of data. Such methods of calibration include linear regression, multiple-linear regression, partial linear regression, and principal components analysis. In other applications, calibrations can be carried out using artificial neural networks, genetic algorithms and rotated principal components.

Instrumentation that detects information for one or more constituents in a complex chemical matrix must rely upon analysis algorithms (such as those derived using chemometrics) in order to reveal information that is specific for one or more chemical constituent. Chemometric techniques can be used to compare unknowns with calibrated standards and data bases to provide advanced forms of cluster analysis, and to extract features from an unknown sample that can be used as information in statistical and mathematical models.

In the practice of the invention, quantitative determinations of chemical analyte concentration using information from UV-vis-NIR spectroscopy can be made using computer algorithms, the parameters of which are determined using chemometric calibration sequences termed "learning sets." Learning sets are generally based on a large number of known (e.g., reference) samples that are used to determine the parameters of the algorithm. The number of samples that are required in any one learning set will be a function of the complexity of the sample matrix and of the number of spectroscopic interferences that are present. Other considerations include the number of dependent variables that will be used in the algorithm. As a general rule, the number of samples in a learning set should be at least ten times the number of dependent variables employed. In the presence of known and unknown interferences, multiple sample calibration seeks to minimize the effects of interferences. Thus, the learning set solutions typify the interferences and variability that will be experienced in actual measurements.

Principal component analysis (PCA) is one method of data reduction which can be performed in the application of chemometric techniques to spectroscopic measurement of chemical analytes in a complex matrix. PCA is used to reduce the dimensionality of a large number of interrelated variables while retaining the information that distinguishes one component from another. This reduction is effected using an eigenvector transformation of an original set of interrelated variables (e.g., an absorption spectrum) into a substantially smaller set of uncorrelated principal component (PC) variables that represents most of the information in the original set. The new set of variables is ordered such that the first few retain most of the variation present in all of the original variables. See, e.g., Jolliffe, L. T., *Principal Component Analysis,* Sprinter-Verlag, New York (1986). More particularly, each PC is a linear combination of all the original measurement variables. The first is a vector in the direction of the greatest variance of the observed variables. The succeeding PCs are chosen to represent the greatest variation of the measurement data and to be orthogonal to the previously calculated PC. Therefore, the PCs are arranged in a descending order of importance.

The term "weighting constant" is meant to include, among other techniques known in the art, the wavelength coefficients of partial least squares regression and/or principal component regression, or any constant obtained from any statistical calibration that can be used to calculate values (such as analyte concentration) for unknown samples. A "wavelength weighting factor" is an embodiment of a weighting constant which is used in the construction of an optical transfer cell or optical filter means capable of extracting wavelength-specific information from spectral data. The wavelength-specific information can be used to determine desired values relating to the sample undergoing analysis (e.g., analyte concentration). A wavelength weighting factor can be embodied as a particular filter density (e.g., neutral or wavelength-specific), filter thickness, or the like, such parameters having been determined using the above-described statistical calibration techniques.

The term "optical transfer cell" encompasses any optically active element that partially absorbs incident radiation in the visible, ultraviolet, or infrared spectral regions, and wherein the absorption is selective with respect to wavelength. For the purposes of the present invention, an optical transfer cell generally comprises an optical filter means having absorption characteristics that were derived from a partial least squares or principal component regression analysis. The optical filter means is used to selectively pass one or more wavelengths from a radiation source, said wavelengths having high correlation with a selected analyte concentration. "High correlation," or "close correlation" refers to the quantitative association between the absorption spectrum at a particular wavelength and a particular analyte concentration, wherein the two variables have a correlation coefficient (r) of 0.9 or higher.

"Correlation spectrometry" refers to a spectrometric method wherein radiation is passed through a sample cell containing an unknown amount of an analyte of interest, and a reference cell that contains a specified amount of the analyte which is to be measured. By detecting the intensity of radiation which has passed though each cell, a signal which is representative of the difference in the radiation intensities can be generated, wherein that difference is proportional to the analyte concentration in the sample.

A "negative correlation filter" is provided when the sample cell used in correlation spectrometry comprises an optical filter having an absorption spectrum that is sufficient to block radiation over a selected bandwidth corresponding to the maximum expected concentration range of the analyte being measured. Thus, as the level of the analyte changes in a sample, the radiation passing through the negative correlation filter remains unaffected, as the filter has blocked all of the radiation in the analyte-specific absorption bands.

A "positive correlation filter" is provided when the sample cell used in correlation spectrometry comprises an optical filter having an absorption spectrum sufficient to pass radiation of a particular wavelength corresponding to the target analyte and not to other absorbing analytes. Thus, the positive correlation filter provides an optimal transfer function that is highly correlated with the analyte concentration in the sample being measured. An ideal positive correlation filter would correlate perfectly with a target analyte (i.e., the correlation coefficient r would be +1.0), and not correlate at all with all other interfering absorbing analytes in a particular sample (r would be 0.0). The synthesis of positive correlation filters is carried out herein using chemometric techniques to determine appropriate wavelength weighting factors as described above.

A "neutral density filter" refers to a standard optical filter means having a flat absorption spectrum. A neutral density filter can be used in concert with correlation filters in a filter system to provide a weighting factor to attenuate absorbances due to the analyte of interest at selected wavelengths and further improve the accuracy of the correlation provided by the system. A neutral density filter can have an absorption spectrum sufficient to attenuate radiation equally at all wavelengths in the range of interest. A reference cell used in correlation spectrometry can comprise a neutral density filter.

As used herein, an "aqueous medium" encompasses any substrate relating to, made from, or comprising water. Thus, an aqueous medium includes mediums wherein water is the major component, where water is present in an amount of about 50%, and solutions wherein water is a solvent but is present in amounts of less than about 50%. Aqueous mediums are specifically defined herein to include mammalian tissue.

The term "blood analyte" refers to a blood constituent that is absorbing in the near-IR range, the measurement of which is useful in patient monitoring or in the provision of health care.

As used herein, the term "near infrared" or "near-IR" encompasses radiation in a spectrum ranging from about 660 to about 3000 nm, more preferably from about 1050 to about 2850 nm, and most preferably from about 1100 to about 2500 nm.

The term "background absorption" relates to the overall or base level of optical absorption of an aqueous sample which is to be analyzed, from which the absorption of a selected constituent departs at one or more characteristic wavelengths to an extent indicative of the concentration of the selected constituent. When the level of background absorption is high in relation to the characteristic absorption of the selected constituent, such as in complex aqueous media where numerous interfering constituents are found, accurate measurement of the magnitude of a slight change in the absorption at the characteristic wavelength of a constituent of interest requires application of the chemometrics techniques described herein. This is particularly so in applications wherein the overall concentration of the constituent of interest is low relative to the aqueous medium (e.g., in the measurement of blood analyte constituents).

GENERAL METHODS

In complex spectral backgrounds such as those present in the spectral analysis of animal tissue or blood samples, interfering substances can produce significant measurement errors. Thus, a primary object of the present invention is to design an optically active element (e.g., an optical transfer cell, or positive correlation filter system) to provide the optimal wavelength weightings for accurate analyte estimation. Synthesis of the optimal positive correlation filter can be achieved according to the invention using two mathematical techniques, rotated principal components (RPC) analysis and least squares analysis.

A. Rotated Principal Components Analysis Method

RPC analysis uses an eigenvector transformation of the original spectrum to provide a set of orthogonal uncorrelated principal component (PC) variables. These PCs are then individually correlated with a target analyte. Through a series of orthogonal rotations, these principal components are then transformed so that a single, rotated PC contains all of the information for a particular target analyte (maximum r) and the other principal component contains no information (r=0). The parameter vector relating this rotate PC to the original spectrum provides the wavelength weighting factors for the optimal positive correlation filter.

1. Eigenvector Transformation

Eigenvector analysis (or principal components analysis) involves the rotation of an original data vector (X) to form a new data vector (X') which can be expressed as $$X'=AX$$

wherein A=an m×m matrix, and m=the number of elements in the original vector (X).

The matrix (A) is derived from the covariance matrix or the correlation matrix of a set of representative samples from a data population of interest. The covariance matrix is calculated from a sample data set. This covariance matrix is then transformed by a process of diagonalization into a new PCs matrix in which the rows of the matrix are ordered by a set of roots known as eigenvalues. The horizontal vectors of this new matrix (A) are called eigenvectors. The subject matrix can be used to transform an original spectral data vector into a transformed vector of independent uncorrelated variables. In this regard, the concept of independence is critical in near-IR spectral analysis of a complex chemical sample (such as blood) in order to remove the effects of interfering chemical analytes. Uncorrelated variables that relate to particular analytes serve as the vehicles of accurate estimations of the analyte concentration.

The above-described transformation does not provide uncorrelated variables that are specific to a particular analyte. Rather, it generates uncorrelated variables of decreasing levels of variance that correlate to varying degrees with a number of different analytes.

2. Principal Component Rotation for Maximal Analyte Correlation

Typically, two to four of the PCs derived from the above PC analysis account for 85–98% of the variance in the original variables. These high variance variables are not necessarily strongly correlated with a particular analyte. Other analytes or matrix effects may contribute greater changes in absorbances. A correlation matrix of a dependent variable analyte provides a convenient basis to rotate a series of PC pairs to produce a single revised PC that more completely "explains" a particular analyte. The revised PCs that relate to a particular analyte will thus supply the parameters for accurate estimation of analyte concentrations.

Each pair of PCs defines a plane. The two PCs that define the plane can be rotated with the purpose of converting the two PCs into a single PC with all of the information content of the original PC pair. One method of completing this conversion is to implement the following computational procedure.

First, the two highest correlated PCs for a particular analyte are selected. This PC pair is rotated until one PC contains all of the information content of the original pair. The rotation angle may be iteratively determined using an exhaustive experimental sequence or it may be analytically determined without iteration. Thus, for $PC'_1$: $R'^2_1+R^2_2$, and for $PC'_2$: $R'_2=0$.

Continuing with the procedure, the next highest correlated PC ($PC_3$) is selected and rotated with $PC'_1$ until, for $PC'_3$: $R'^2_3=R^2_3+R'^2_1$, and for $PC'_1$: $R'^2_1=0$.

The above rotational sequence is repeated until all of the analyte correlating vectors have been treated. The single, rotated PC generated by the rotational sequence contains all of the information for a particular target analyte (maximum r) and the other PC contains no information (r=0). Further, the subject PC is independent of the absorbance contributions produced by other optically active analytes in the sample. The parameter vector relating this rotated PC to the original spectrum provides the wavelength weighting factor for the optimal positive correlation filter (optical transfer cell).

B. Least Squares Analysis Method

In the application of the least squares method, the optimal transfer function is obtained directly. Given a collection of vectors, $x_i$, wherein i=1, n, a vector (v) must be found such that $x_i^T v$ will lie as close as possible to a line when $x_i^T v$ is plotted against $c_i$ (the concentration value for $x_i$). Thus, a and b must also be found, such that $ax_i^T v + b = c_i$, for all i.

Since equality cannot be actually attained, a minimum must be accepted, in a least squares sense, of $\|ax_i^T v + b - c_i\|$, for all i.

Thus, the problem is formulated as follows. A matrix (A) is formed:

$$A = \begin{pmatrix} x_1^T \\ x_2^T \\ \cdot \\ \cdot \\ \cdot \\ x_n^T \end{pmatrix}$$

and vectors $$C = \begin{pmatrix} c_1 \\ c_2 \\ \cdot \\ \cdot \\ \cdot \\ c_n \end{pmatrix} \quad \bar{b} = \begin{pmatrix} b_1 \\ b_2 \\ \cdot \\ \cdot \\ \cdot \\ b_n \end{pmatrix}$$

When the objective function is rewritten as $\min (a, \bar{b}, v) = \|aAv + \bar{b} - c\|$, and by letting $\bar{v} = av$, the above function decreases to $\min \bar{v}, \bar{b} \|A\bar{v} + \bar{b} - c\|$.

Now, defining $$\bar{A} = \begin{pmatrix} A \\ \bar{b}^T \end{pmatrix} \bar{\bar{v}} = \begin{pmatrix} \bar{v} \\ 1 \end{pmatrix},$$

the problem becomes $\min (\bar{v}) = \|\bar{A}\bar{\bar{v}} - c\|$.

This relationship is well known and has the solution $\bar{\bar{v}} = (\bar{A}^T \bar{A})^{-1} \bar{A}^T C$ The vector $(\bar{v})$ is thus the optimal weighting function to implement the optical transfer function in the positive correlation filter.

Determined over a large number of samples, both the rotated principal components and the least squares analysis methods will likely produce substantially similar optical transfer functions. However, for more limited sample sets, the rotated principal components methods will be more effective due to the orthogonal nature of the optimal transfer function. The transfer functions are then used to determine the parameters for the positive correlation filters of the present invention.

The aforementioned positive correlation filters are employed herein in a variety of devices configured to extract analyte concentration information from complex spectral media using near-IR spectrometer devices. A number of near-IR spectrometers, Fourier Transform near-IR spectrometers, and modified IR spectrometers of conventional design can be used in the practice of the invention. The preferred mode of operation is reflectance. Suitable spectrometers include the NIR-Systems model 5000 analyzer, available from Perstorp Analytical (Silver Spring, Md.), and the Luminar 2000 analyzer, available from Brimrose (Baltimore, Md.). The techniques for sampling, measuring, and signal processing can be conventional and are well known to those of skill in the art.

Figure 1:
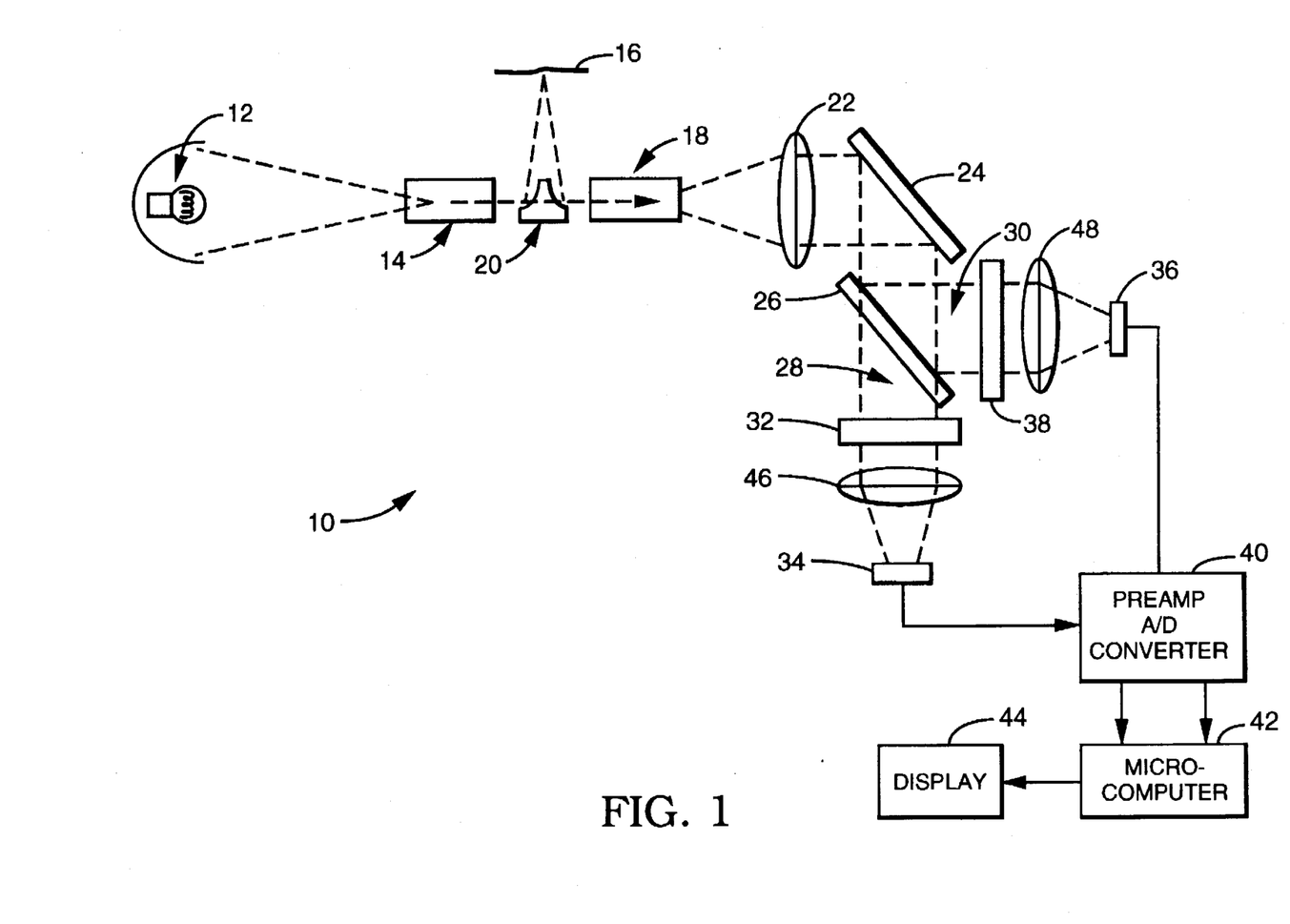
FIG. 1 is a diagrammatic representation of one embodiment of a correlation spectrometer constructed according to the invention.

Referring now to FIG. 1, an apparatus for measurement of analyte concentration in a complex aqueous medium is generally indicated at 10. The apparatus includes a radiation source 12 which is capable of generating a spectrum of near infrared (near-IR) radiation within the range of approximately 600 to approximately 2500 nm. A number of suitable radiation sources are known in the art, such as incandescent light sources directed across interference filters, halogen light sources (modulated by an associated chopper wheel), laser light sources, laserdiode arrays, or high speed light-emitting diode (LED) arrays.

Radiation from the source 12 is directed to sample interface optic means 14 which reflectively transmits the radiation to a medium 16 containing the blood analyte of interest. After the radiation has interrogated the medium, spectrally modified radiation is transmitted back to the apparatus 10 through further sample interface optic means 18. The apparatus 10 can be designed to closely interface with the medium 16, such as where the radiation is directed to the medium and modified radiation transmitted back to the apparatus using an optically active means 20 (e.g., light converging means such as a lens, or beam deflection optics) known in the art. Alternatively, the sample interface optic means 14 and 16 can comprise fiber optic waveguides coupled to the apparatus in order to enable more remote medium interfacing. Other configurations are provided wherein a single fiber optic bundle is employed to transmit the radiation to and from the medium. An optrode disposed at the end of the single bundle transmits the near-IR radiation to the sample medium 16 and receives spectrally modified radiation therefrom which is directed back through the bundle to the apparatus 10. Sapphire or high-grade quartz can be used as optical elements in the above fiber optic waveguides, as those materials have very good transmission characteristics in the near-IR spectral range. Other suitable fiber optic waveguides include fluoride-based systems known in the art.

In each of the above-described configurations, radiation from sample interface optic means 14 is directed to the medium 16 where the near-IR radiation interacts with the constituents of the sample and is absorbed, dispersed, diffused and reflected. This spectrally modified radiation is then collected and directed to the apparatus 10.

The spectrally modified radiation transmitted by sample interface optic means 18 is then directed to a means 22 for receiving and directing the radiation into a beam path, such as a collimating lens or the like. The beam path communicates with means 24 for passing selected wavelengths, such as a diffraction grating system or selective filtering means. Use of a diffraction grating system serves to eliminate wavelengths not having a relationship to the analyte of interest, and divides the radiation into distinct wavelengths. Radiation passing through the means 24 is directed through a beam splitter 26, whereby the radiation is divided into two beams, respectively indicated at 28 and 30. Suitable beam splitter means include mirror configurations such as those known in the art.

A first beam 28 from beam splitter 26 is communicated with an optical transfer cell 32 which is disposed in the beam path. The optical transfer cell 32 comprises a positive correlation filter system having absorption spectra sufficient to accept the spectrally modified near-IR radiation from the beam 28 and selectively pass one or more wavelengths therefrom having high correlation with a selected analyte concentration. The positive correlation filter system includes one or more optically active filter means having absorption characteristics determined using a partial least squares or principal component regression of an original spectrum of a sample containing an analyte of interest.

Positive correlation filter systems can be constructed using a suitable substrate layer that is capable of transmitting radiation at least in the 1100–2500 nm range. The substrate layer is generally coated with one or more layers of metals and/or oxides that are conventional in the art. Such coatings can be applied to the substrate using emulsion or chemical vapor deposition (CVD) techniques well known in the art. In preferred embodiments, the positive correlation filter system comprises a photographic mask with spectral lines of optical density proportional to an optimal weighting function determined using rotated principal components or least squares analysis methods. One particular filter system has a filter density and/or thickness that comprises a wavelength weighting factor means, wherein the weighting factor provides enhanced positive correlation of a passed wavelength with the concentration of an analyte in the selected sample medium. The weighting factor means is an embodiment of a weighting constant determined using chemometrics, wherein the constant allows for the construction of an optical filter that is able to extract wavelength-specific information from spectral data. The wavelength-specific information can then be used to readily determine analyte concentration.

Thus, the optical transfer cell 32 allows for the measurement of analyte concentration in a variety of complex mediums, such as any aqueous medium having a complex spectral background (e.g., in which interfering constituents in the medium can produce significant measurement errors). Particularly, the optical transfer cell 32 finds use in applications where there exists significant background absorption from which the absorption of a specific constituent of interest departs at one or more characteristic wavelengths to an extent indicative of the concentration of that constituent. When the level of the constituent of interest is low relative to the medium, the need for such an optical transfer cell becomes more acute.

In one application, the optical transfer cell 32 can be used in the determination of blood analyte concentrations. The blood analyte can be present in an in vitro sample medium (e.g., a blood sample), or can be present in an in vivo tissue sample. In particular applications, the blood analyte of interest is a blood electrolyte (e.g., calcium, potassium, sodium, chloride and bicarbonate ($CO_2$)), blood hydrogen ion concentration (pH), an organic compound present in blood such as glucose and urea (BUN), or a blood constituent such as hematocrit or hemoglobin. In each of the aforementioned devices, the optical transfer cell 32 includes a positive correlation filter system that has been synthesized for the determination of the concentration of the specific analyte of interest. As will be readily appreciated by those of skill in the art, the optical transfer cell can be detachably mounted in the apparatus 10, whereby a variety of different cells can be cassetted into and out of the apparatus when one is desirous of quantifying different analytes.

Referring still to FIG. 1, the correlated wavelengths passed by optical transfer cell 32 are received by a detection means 34 for converting the optical information (correlated wavelengths) into a signal that is representative of the intensity of that information. In one particular apparatus, the detection means 34 comprises a lead sulfide (PbS) photodetector able to scan the range of wavelengths from about 1100 to at least about 2500 nm in steps of 1 nm. Such detection means convert the passed radiation (wavelengths) into signals representative of the intensities of those wavelengths.

A second beam 30 from beam splitter 26 is communicated to a further detection means 36, whereby the spectral information is converted into signals representative of the intensity thereof. The second beam 30 of spectrally modified radiation may pass through a reference optical transfer cell 38 disposed in the path of said beam. The reference cell 38 can comprise a neutral density filter means having absorption characteristics sufficient to attenuate radiation equally over a selected range of near-IR wavelengths. The signals from detection means 34 and 36 are communicated a means 40 for converting those signals into digital signals, e.g, digital signals indicative of the differences between the correlated wavelengths emerging from the positive correlation filter and the attenuated wavelengths emerging from the neutral density filter. More particularly, the signals are communicated to an analog/digital (A/D) converter for conversion to digital form. The digital information is then readily input into a microprocessor 42 to calculate actual analyte concentration. The concentration can conveniently be visualized through a digital display means 44.

Various optional components for use in the apparatus 10, such as first and second radiation focusing means, respectively indicated at 46 and 48 and capable of receiving and directing the radiation emerging from optical transfer cells 32 and 38 into a beam path, will be apparent to those skilled in the art. In some apparatuses, such focusing means can comprise a focusing lens or the like. Alternatively, the apparatus 10 can include, for example, a single detection means capable of receiving spectral information from the split beams 28 and 30.

Figure 2:
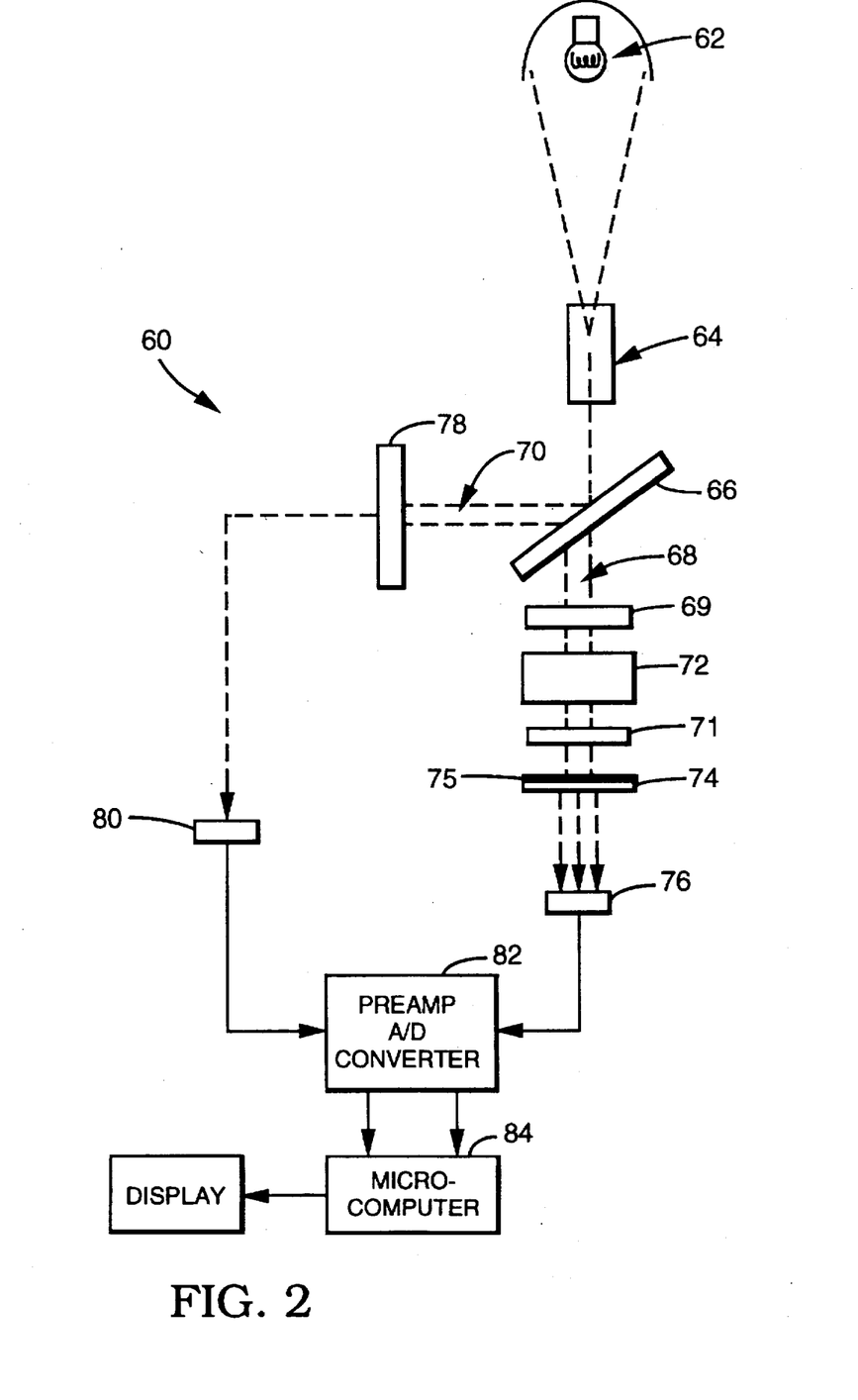
FIG. 2 is a diagrammatic representation of an alternative embodiment of a correlation spectrometer constructed according to the invention.

Referring now to FIG. 2, an alternative apparatus for measurement of analyte concentration in a complex aqueous medium is generally indicated at 60. The apparatus includes a radiation source 62 which is capable of generating a spectrum of near infrared (near-IR) radiation within the range of approximately 660 to approximately 2500 nm. Radiation from source 62 is transmitted to an optically active means 64 for receiving and directing the radiation into a beam path and/or for passing selected wavelengths, such as a collimating lens, selective filtering means or the like. In one case, the optically active means 64 can comprise a monochromator, wherein a control signal obtained from a microcomputer is used to step the position of the monochromator relative to the beam path.

Near-IR radiation emerging from means 64 is communicated through a beam splitter 66, whereby the radiation is divided into two beams, respectively indicated at 68 and 70. The first beam 68 from beam splitter 66 is transmitted to a sample medium 72 containing an unknown concentration of an analyte of interest. In FIG. 2, the sample medium 72 comprises a sample cell formed from a suitable substrate capable of transmitting radiation in the near-IR range of interest. In one case, the sample can comprise a blood serum sample, wherein it is desired to determine the concentration of blood analytes. Alternatively, the first beam 68 can be transmitted to a sample surface such as a tissue surface using direct interfacing means or indirect interfacing means (e.g., fiber optic waveguides means) 69 as have been described supra. In this manner, the concentration of blood analytes present in the tissue sample can be non-invasively determined using reflective near-IR measurement 71 of the absorption spectrum of radiation which has interacted with the tissue sample.

Spectrally modified radiation that has interacted with the constituents of the sample (including the analyte of interest) is then collected and directed to an optical transfer cell 74 which is disposed in the beam path. The optical transfer cell 74 comprises a positive correlation filter system having an absorption spectrum sufficient to accept the radiation and selectively pass one or more wavelengths therefrom having high correlation with the concentration of an analyte of interest, and substantially no correlation with interfering components present in the sample. Radiation emerging from the optical transfer cell 74 is received by a detection means 76 for converting the spectrally modified radiation into a signal that is representative of the intensity of that radiation. The detection means can comprise a broad spectrum photodetector such as an PbS photodetector or the like.

Referring still to FIG. 2, the second beam 70 from beam splitter 66 is transmitted to an optically active element 78 which is disposed in the beam path. In one configuration, the optically active element 78 comprises a neutral density filter means having absorption characteristics sufficient to attenuate radiation equally over a selected range of near-IR wavelengths. In an alternative configuration, the optically active element 78 is an optical transfer cell that includes a positive correlation filter system having an absorption spectrum that is identical to the absorption spectrum of optical transfer cell element 74. The radiation emerging from the optically active element 78 is received by a detection means 80 for converting the radiation into a signal that is representative of the intensity thereof.

The positive correlation filter systems can be constructed as described above. Thus, the subject filters can comprise a single substrate layer having an optically active coating which imparts absorption characteristics capable of selectively passing one or more wavelengths having high correlation with a particular analyte concentration. In preferred embodiments, the positive correlation filter system comprises a plurality of filter layers, each layer having a selected filter density and/or filter thickness suitable to provide a desired absorption characteristic. In one case, at least one layer 75 of the system has a filter density and/or thickness that comprises a wavelength weighting factor means, wherein the weighting factor provides enhanced positive correlation of a passed wavelength with the concentration of an analyte in the selected sample medium.

The signals generated by detection means 76 and 80 are then communicated to a means 82 for converting those signals into a digital signal indicative of the ratio of the intensity of the radiation emerging from the source 62 and the corresponding spectrally modified radiation emerging from the sample. In this manner, changes in the intensity of the radiation emerging from the source 62 can be corrected for, eliminating a potential source of error in the measurement obtained from the system. Further, the ratio of the signals can then be converted to digital form and interpreted to determine analyte concentration using an internal microprocessor 84 system or an associated system using methods known in the art.

In particularly preferred embodiments, the microprocessor calculates analyte concentration by application of a chemometrics algorithm to the ratio signal. The appropriate algorithm can be determined using the above-described chemometrics techniques, such as a least squares analysis or rotated principal component analysis of an original absorption spectrum of the analyte of interest.

In a further aspect of the invention, a non-invasive method of measuring the concentration of a blood analyte is provided. The method generally employs a near-IR spectrometer apparatus such as those described above. Particularly, a method is provided wherein near-IR radiation is directed to a medium containing a blood analyte of interest. In one case, the radiation is caused to impinge upon the skin surface of tissue, such as upon a subject's forearm. The radiation is directed at an angle toward the tissue such that it is absorbed by the tissue material near the surface and reflected as diffuse radiation. In this manner, the radiation is spectrally modified as a result of infrared absorptions by the blood and tissue constituents. Portions of the interrogating near-IR radiation are absorbed, dispersed, diffused and reflected from the blood constituents contained within the tissue source. This spectrally modified radiation contains information specific for each optically active blood constituent. However, due to the complexity of the chemical and physical matrix of the tissue, a large amount of background spectral information is also obtained which must be removed or accounted for in order to extract analyte-specific information. The near-IR radiation used to interrogate the medium preferably includes radiation in the range of approximately 1100 to 2500 nm.

In a further preferred aspect of the invention, a non-invasive method is provided for determining blood glucose levels using the above-described transcutaneous forearm measurement techniques. The vibrational motion of the blood glucose molecules can be measured using diffuse-reflective near-IR radiation, wherein the vibrational motion includes both rotational and translational motion, including overtone vibrations and combined vibrations. Of these vibrations, the overtone vibrations are dominant.

Such transcutaneous, reflective measurements carried out in the forearm area provide a more uniform representation of blood glucose than prior methods that are carried using transmissive near-IR finger measurements. Near-IR light transmission in the finger area interacts with a mixture of arterial, venous and capillary blood, as well as bone, cartilage and other subcutaneous material. On the other hand, reflective arm measurements are limited to capillary blood (and interstitial fluid) almost exclusively. Since capillary, venous and arterial blood glucose concentrations are known to differ slightly, the measurement of a single blood state (e.g., in transcutaneous forearm measurements) provides for a more consistent monitor of blood glucose. Reflective arm measurements are also much less sensitive to sensor location placement than transmissive finger measurements, wherein variation of sensor placement and rotation can lead to errant spectral measurements. Furthermore, skin pigmentation variations from racial and individual differences cause absorption variations in the transmissive near-IR region (e.g., 800 to 1000 nm), but not in the reflective near-IR region (e.g., over 1000 nm).

In each of the above methods, the near-IR radiation that was directed to the medium containing the analyte of interest is caused to be reflected by the medium to provide a spectrally modified beam of radiation. This spectrally modified radiation is directed into a path through an optical transfer cell disposed within the beam path. The optical transfer cell comprises a positive correlation filter system, as has been described in detail above.

Accordingly, the invention provides a positive correlation filter system configured to accept the beam of spectrally modified near-IR radiation and selectively pass one or more wavelengths therefrom. The passed wavelengths are selected to have high correlation with an analyte concentration. The methods further entail measuring the intensity of the passed wavelengths and generating a signal representative of the intensity of the wavelengths. The resultant signal can then be converted into an indication of analyte concentration using methods known in the art. In a preferred embodiment, the analyte concentration is determined using an application of a chemometrics algorithm to the resultant signal.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

Transcutaneous near-IR reflective measurement of blood analyte concentrations was carried out in parallel with actual laboratory testing of patient blood samples to evaluate the accuracy of such methods and to develop training set data for the above described chemometric techniques. More particularly, a near-IR photodiode array analyzer operating reflectively in the 1100–1800 nm range was used to test two separate patient populations (at the Bethesda Naval Hospital (Maryland) and the Froedtert Lutheran Memorial Hospital (Milwaukee), respectively). The testing apparatus employed a halogen light source that was coupled to an optical fiber means through a shutter and attenuator means. The shutter means allowed for light blocking sufficient to provide for a dark reading of the associated photodetector array. Near-IR radiation in the 1100–1800 nm spectral region was transmitted to a reflective optical probe that was coupled to the patient skin surface (in the forearm area). Diffuse back-scattered radiation that had penetrated the epidermis and dermis was collected by a receiving optical fiber means that transmitted the radiation to a spectrograph where it was detected by an indium gallium arsenide photodetector array (256×1) and converted to digital form by array interface electronics. The spectral signals were then interfaced to a microcomputer for signal processing and pattern recognition.

The results of the non-invasive transcutaneous analysis of the following blood electrolyte analytes: calcium ($CA^+$), potassium ($K^+$), sodium ($NA^+$), chloride ($CL^-$) and bicarbonate ($CO_2^-$); blood glucose (GLU), blood urea (BUN); hematocrit (HCT) and hemoglobin (HEM) are set forth in Table I. An effective measurement is characterized by a small average error, a slope (b) approaching 1.0 and a high T-value (T). The slope is defined as the tangent of the least square fit line of predicted values/actual values. The predicted values were obtained using the transcutaneous measuring apparatus of the invention and the actual values were obtained by physical laboratory testing of patient blood samples. The T-value can be described as a "tracking value" that indicates how well the predicted value tracked with changes in the actual value. The T-value is defined as the slope/standard error of the slope.

TABLE I

| Analyte | Mean Value | Range | Average Error | (b) | T |
|---|---|---|---|---|---|
| $CA^+$ mg/dl | 9.63 mg/dl | 8.5–10.6 | 0.21 mg/dl 2.18% | 0.57 | 7.01 |
| $K^+$ mmol/L | 4.44 mmol/L | 3.5–5.5 | 0.16 mmol/L 3.60% | 0.75 | 10.82 |
| $NA^+$ mmol/L | 140.51 mmol/L | 135–148 | 1.24 mmol/L 0.88% | 0.59 | 6.95 |
| $CL^-$ mmol/L | 103.68 mmol/L | 94–110 | 1.13 mmol/L 1.09% | 0.57 | 9.56 |
| $CO_2^-$ mmol/L | 28.56 mmol/L | 22–35 | 1.55 mmol/L 5.43% | 0.46 | 4.12 |
| GLU mg/dl | 98.07 mg/dl | 60–115 | 13.97 mg/dl 14.24% | 1.00 | 14.61 |
| BUN mg/dl | 15.58 mg/dl | 7–26 | 1.99 mg/dl 12.77% | 0.67 | 9.17 |
| HCT % | 41.78% | 33–55 | 2.62% 6.27% of mean | 0.41 | 5.94 |
| HEM g/dl | 14.32 g/dl | 12–18 | 0.89 g/dl 6.22% | 0.48 | 6.45 |

EXAMPLE 2

The Transcutaneous near-IR reflective measurements of blood analyte concentrations carried out in Example 1 were repeated using a additional 500 patients at the Naval Hospital in San Diego, Calif. The data generated were used to carry out a training set/test set sequence using the chemometric methods of the present invention. The results of a "leave-one-out" principal component regression analysis of the following blood electrolyte analytes: calcium ($CA^+$), potassium ($K^+$), sodium ($NA^+$), chloride ($CL^-$) and bicarbonate ($CO_2^-$); blood glucose (GLU), blood urea (BUN); hematocrit (HCT) and hemoglobin (HEM) are set forth in Table II. Once again, an effective measurement is characterized by a small average error, a slope (b) approaching 1.0 and a high T-value (T). The predicted values were obtained using the transcutaneous measuring apparatus of the invention and the actual values were obtained by physical laboratory testing of patient blood samples.

TABLE II

Leave-One-Out Estimation Results, 10 Variables
Principal Component - Multiple Regression Estimation

| Analyte | Data Set Characteristics | | | Learning Set | | | | Test Set | | | |
|---|---|---|---|---|---|---|---|---|---|---|---|
| Name | Min | Max | Mean | Ave Error | % Error | Slope (b) | T | Ave Error | % Error | Slope (b) | T |
| NA+ mmol/L | 132 | 147 | 139.5 | 2.38 | 1.71 | 0.12 | 7.67 | 2.43 | 1.74 | 0.095 | 6.10 |
| CL– mmol/L | 95 | 110 | 102.7 | 2.33 | 2.27 | 0.15 | 8.71 | 2.39 | 2.33 | 0.12 | 7.28 |
| K+ mmol/L | 3.5 | 5.5 | 4.50 | 0.348 | 7.73 | 0.13 | 8.11 | 0.355 | 7.89 | 0.11 | 6.61 |
| CA mg/dl | 8.4 | 10.4 | 9.42 | 0.324 | 3.44 | 0.15 | 8.93 | 0.332 | 3.52 | 0.13 | 7.52 |
| CO2 mmol/L | 21 | 32 | 26.7 | 1.98 | 7.42 | 0.15 | 9.08 | 2.03 | 7.6 | 0.13 | 7.67 |
| BUN mg/dl | 6 | 37 | 16.17 | 4.11 | 25.42 | 0.20 | 10.52 | 4.21 | 26.04 | 0.18 | 9.24 |
| HCT % | 32 | 51 | 41.3 | 3.02 | 7.31 | 0.16 | 9.06 | 3.10 | 7.51 | 0.14 | 7.64 |
| GLU mg/dl | 60 | 164 | 98.47 | 14.07 | 14.29 | 0.15 | 8.45 | 14.45 | 14.67 | 0.12 | 6.96 |
| HEM g/dl | 10.8 | 17.4 | 14.16 | 1.02 | 7.20 | 0.15 | 8.81 | 1.05 | 7.42 | 0.15 | 8.81 |

I claim:

1. An apparatus for measurement of analyte concentration in a sample, comprising:

(a) a source of near infrared radiation;

(b) means for dividing radiation emerging from the source into first and second beam paths;

(c) optical filtering means disposed in the second beam path and having absorption characteristics sufficient to attenuate the intensity of the radiation in said second beam path;

(d) means for receiving attenuated radiation from the optical filtering means and for converting the same into signals representative of the intensity thereof;

(e) means for irradiating the sample with the first beam path of radiation and obtaining reflected radiation emerging from the sample;

(f) means for collecting the reflected radiation and directing said reflected radiation to an optically active element that comprises a positive correlation filter having a plurality of filter layers each capable of accepting the reflected radiation and selectively passing a wavelength therefrom, wherein each selectively passed wavelength has high correlation with the analyte concentration;

(g) means for receiving radiation at selectively passed wavelengths from the optically active element and for converting the same into signals representative of the intensity thereof; and (h) means for calculating the concentration of the analyte in the sample using the signals generated by parts (d) and (g).

2. The apparatus of claim 1, wherein the optical filtering means of part (c) comprises a neutral density filter having absorption characteristics sufficient to attenuate the intensity of the radiation in the second beam path equally over a selected range of near infrared wavelengths.

3. The apparatus of claim 1, wherein the optical filtering means of part (c) comprises a second optically active element having a second positive correlation filter substantially identical to that of the positive correlation filter of part (f).

4. The apparatus of claim 1, wherein the means for calculating analyte concentration comprises the conversion of the signals generated by parts (d) and (g) into a digital signal which represents the ratio of the intensities thereof.

5. The apparatus of claim 4, wherein the means for calculating analyte concentration further comprises application of a chemometrics algorithm to the ratio of the signals.

6. The apparatus of claim 1, wherein at least one layer of the positive correlation filter further comprises wavelength weighting factor means, said weighting factor means providing enhanced positive correlation of radiation at a passed wavelength to the analyte concentration in a selected medium.

7. The apparatus of claim 6, wherein each filter layer is adapted to pass a wavelength having high correlation with the concentration of a blood analyte selected from the group consisting of calcium, potassium, sodium, chloride, bicarbonate ($CO_2$), hydrogen ion concentration (pH), glucose, urea (BUN), hematocrit and hemoglobin.

8. The apparatus of claim 1, wherein the near infrared radiation includes wavelengths in the range of approximately 1100 to 2500 nm.

* * * * *